US012084457B2

(12) United States Patent
Dahl et al.

(10) Patent No.: US 12,084,457 B2
(45) Date of Patent: Sep. 10, 2024

(54) METHODS FOR THE PREPARATION OF 1,3-BENZODIOXOLE HETEROCYCLIC COMPOUNDS

(71) Applicant: UNION therapeutics A/S, Hellerup (DK)

(72) Inventors: Allan Carsten Dahl, Ballerup (DK); Johan Eriksson Bajtner, Ballerup (DK); Esben Paul Krogh Olsen, Ballerup (DK); Bjørn Metzler, Ballerup (DK)

(73) Assignee: UNION therapeutics A/S, Hellerup (DK)

( * ) Notice: Subject to any disclaimer, the term of this patent is extended or adjusted under 35 U.S.C. 154(b) by 0 days.

(21) Appl. No.: 17/539,715

(22) Filed: Dec. 1, 2021

(65) Prior Publication Data

US 2022/0162227 A1 May 26, 2022

Related U.S. Application Data

(62) Division of application No. 16/624,491, filed as application No. PCT/EP2018/066229 on Jun. 19, 2018, now Pat. No. 11,220,514.

(30) Foreign Application Priority Data

Jun. 20, 2017 (EP) .................................... 17176767

(51) Int. Cl.
  *C07D 495/10* (2006.01)
  *B01J 21/16* (2006.01)
(52) U.S. Cl.
  CPC ............ *C07D 495/10* (2013.01); *B01J 21/16* (2013.01); *C07B 2200/13* (2013.01)
(58) Field of Classification Search
  CPC .................................................... C07D 495/10
  See application file for complete search history.

(56) References Cited

U.S. PATENT DOCUMENTS

| | | | |
|---|---|---|---|
| 6,094,614 A | 7/2000 | Hiwatashi | |
| 6,169,086 B1 * | 1/2001 | Ejima | C07D 231/12 544/371 |
| 6,549,840 B1 | 4/2003 | Mikami et al. | |
| 6,630,813 B2 | 10/2003 | Berels et al. | |
| 6,716,987 B1 | 4/2004 | Ohshima | |
| 8,338,431 B2 | 12/2012 | Bollu et al. | |
| 8,940,761 B2 | 1/2015 | Nielsen et al. | |
| 8,952,162 B2 | 2/2015 | Nielsen et al. | |
| 8,980,905 B2 | 3/2015 | Nielsen | |
| 9,181,248 B2 | 11/2015 | Nielsen et al. | |
| 9,273,064 B2 | 3/2016 | Nielsen | |
| 9,637,499 B2 | 5/2017 | Nielsen | |
| 9,908,894 B2 | 3/2018 | Metzler et al. | |
| 10,793,580 B2 | 10/2020 | Liang et al. | |
| 10,906,915 B2 | 2/2021 | Liang et al. | |
| 11,065,257 B2 | 7/2021 | Liang et al. | |
| 11,220,514 B2 | 1/2022 | Dahl et al. | |
| 11,292,799 B2 | 4/2022 | Andrews et al. | |
| 11,299,497 B2 | 4/2022 | Larsen et al. | |
| 11,365,204 B2 | 6/2022 | Larsen | |
| 11,370,799 B2 * | 6/2022 | Dahl | C07D 495/10 |
| 11,384,096 B2 | 7/2022 | Andrews et al. | |
| 2003/0203918 A1 | 10/2003 | Meade | |
| 2005/0245750 A1 | 11/2005 | Atsumi | |
| 2008/0015226 A1 | 1/2008 | Amari | |
| 2010/0035908 A1 | 2/2010 | Felding | |
| 2010/0099688 A1 | 4/2010 | Felding et al. | |
| 2012/0028974 A1 | 2/2012 | Nielsen et al. | |
| 2013/0123291 A1 | 5/2013 | Nielson | |
| 2013/0225609 A1 | 8/2013 | Nickolaus | |
| 2014/0329853 A1 | 11/2014 | Nielsen et al. | |
| 2015/0105420 A1 | 4/2015 | Nielsen et al. | |
| 2015/0111915 A1 | 4/2015 | Nielsen | |
| 2016/0022657 A1 | 1/2016 | Nielsen | |
| 2017/0137438 A1 | 5/2017 | Metzler et al. | |
| 2019/0330223 A1 | 10/2019 | Liang et al. | |
| 2020/0010477 A1 | 1/2020 | Liang et al. | |
| 2020/0239493 A1 | 7/2020 | Larsen | |
| 2020/0262842 A1 | 8/2020 | Dahl et al. | |
| 2020/0323869 A1 | 10/2020 | Liang et al. | |
| 2020/0385400 A1 | 12/2020 | Larsen et al. | |
| 2021/0070769 A1 | 3/2021 | Andrews et al. | |
| 2021/0079012 A1 | 3/2021 | Andrews et al. | |
| 2021/0147440 A1 | 5/2021 | Dahl et al. | |
| 2021/0386674 A1 | 12/2021 | Rasmussen et al. | |
| 2022/0281889 A1 | 9/2022 | Larsen | |
| 2022/0362259 A1 | 11/2022 | Liang et al. | |

(Continued)

FOREIGN PATENT DOCUMENTS

| | | |
|---|---|---|
| JP | H03148337 A | 6/1991 |
| JP | 2006/008522 A | 1/2006 |

(Continued)

OTHER PUBLICATIONS

Frey et al., "Practical synthesis of a highly functionalized thiazole ketone", Tetrahedron 2003, 59, pp. 6363-6373.
International Search Report and Written Opinion of the International Searching Authority for International Application No. PCT/EP18/066229 dated Oct. 15, 2018.
International Search Report and Written Opinion for International Application No. PCT/EP2016/081368 dated Feb. 22, 2017.
PubChem CID 54765967 (Jan. 23, 2012).
Robert Ballini et al., Zeolite HSZ-360 as a new reusable catalyst for direct acetylation of alcohols and penols under solventless conditions, Tetrahedron Letters pp. 6049-6052 (1998).
Sperry et al., "A safe and practical procedure for the difluoromethylation of methyl 4-hydroxy-3-iodobenzoate", Org. Process Res. Dev. 15, 2011, pp. 721-725.

(Continued)

*Primary Examiner* — Laura L Stockton
(74) *Attorney, Agent, or Firm* — Mintz, Levin, Cohn, Ferris, Glovsky and Popeo, P.C.

(57) ABSTRACT

The present invention relates to novel methods for the preparation of 1,3-benzo-dioxole heterocyclic compounds. The compounds are useful as PDE4 inhibitors.

21 Claims, 1 Drawing Sheet

(56) References Cited

U.S. PATENT DOCUMENTS

2023/0073362 A1  3/2023  Dahl et al.
2023/0087354 A1  3/2023  Andrews et al.

FOREIGN PATENT DOCUMENTS

| | | |
|---|---|---|
| JP | 2012067143 A | 4/2012 |
| JP | 2012/229192 A | 11/2012 |
| JP | 6850886 B2 | 3/2021 |
| JP | 6850887 B2 | 3/2021 |
| WO | 1996036624 A1 | 11/1996 |
| WO | 2008/077404 A1 | 7/2008 |
| WO | 2008/104175 A3 | 9/2008 |
| WO | 2011/160632 A1 | 12/2011 |
| WO | 2014/096018 A1 | 6/2014 |
| WO | 2015/197534 A2 | 12/2015 |
| WO | 2017/103058 A1 | 6/2017 |
| WO | 2018/234299 A1 | 12/2018 |
| WO | 2019057806 A1 | 3/2019 |
| WO | 2019115776 A1 | 6/2019 |
| WO | 2020148271 A1 | 7/2020 |
| WO | 2022200339 A1 | 9/2022 |

OTHER PUBLICATIONS

Zafrani et al., "Diethyl bromodifluoromethylphosphonate: a highly efficient and environmentally benign", Tetrahedron 65, 2009, pp. 5278-5283.
Zhang et al., "2-chloro-2,2-difluoroacetophenone: a non-ODS-based difluorocabene precursor and its use in", J. Org. Chem. 2006, 71, 9845-9848.
Zheng et al., "Chlorodifluoromethyl phenyl sulfone: a novel non-ozone-depleting substance-based", Chem. Commun. 2007, 5149-5151.
International Search Report and Written Opinion for International Application No. PCT/EP2015/063942, dated Jan. 26, 2016, 11 pages.
Yanagisawa et al. (Jan. 4, 2011) "Process Development of the PDE4 Inhibitor K-34", Organic Process Research & Development, 15:376-381.

* cited by examiner

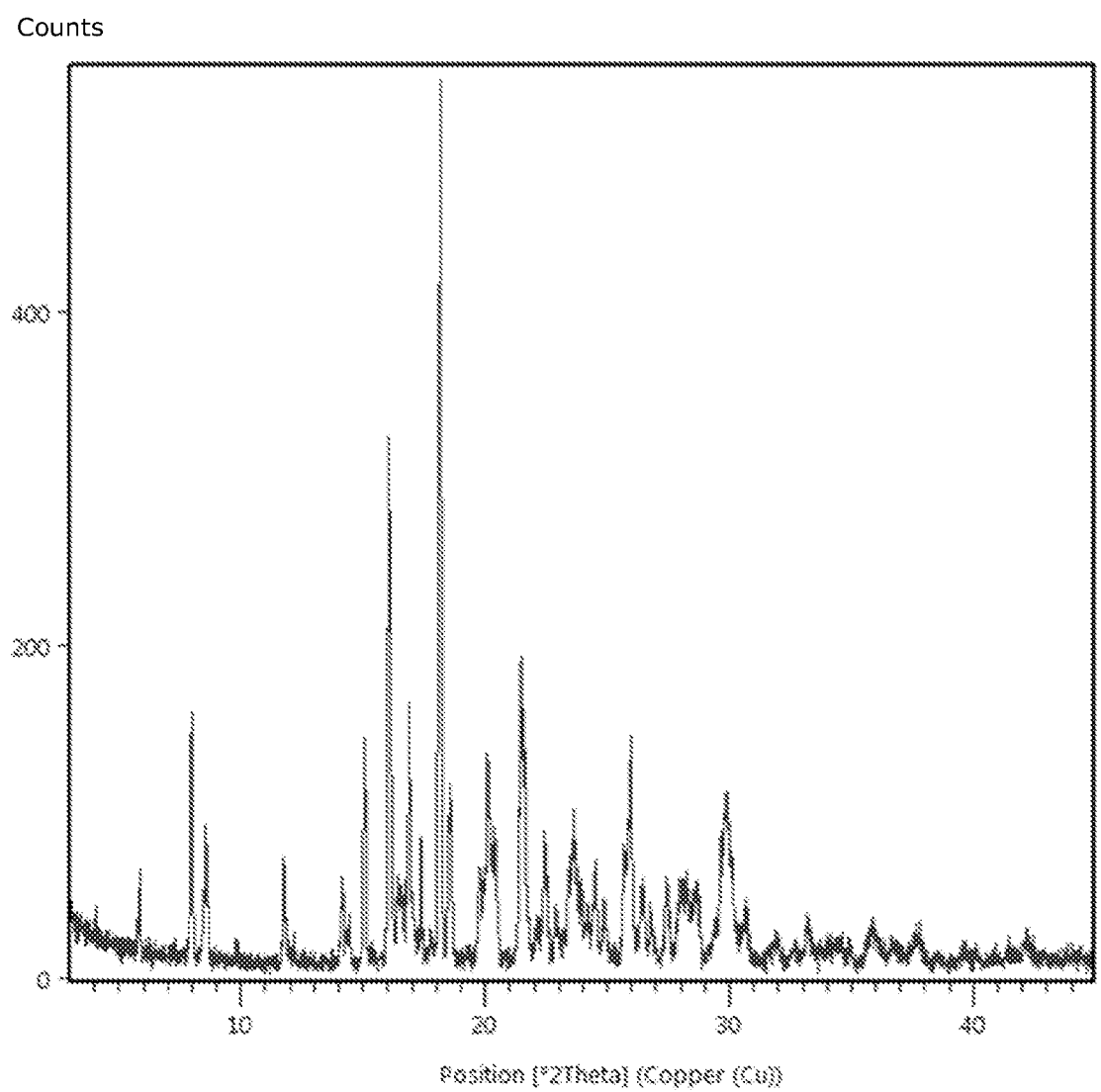
Graph 1. XRPD pattern of Crystalline form (E) of 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone

METHODS FOR THE PREPARATION OF 1,3-BENZODIOXOLE HETEROCYCLIC COMPOUNDS

CROSS-REFERENCE TO RELATED APPLICATIONS

The present application is a Divisional of U.S. application Ser. No. 16/624,491, filed Dec. 19, 2019, now U.S. Pat. No. 11,220,514, which is a U.S. national stage filing under 35 U.S.C. § 371 of International Application No. PCT/EP2018/066229, filed Jun. 19, 2018, which claims priority to European Patent Application No. 17176767.6, filed Jun. 20, 2017, the disclosures of which are herein incorporated by reference in their entirety.

FIELD OF THE INVENTION

The present invention relates to novel methods for the preparation of 1,3-benzo-dioxole heterocyclic compounds. The compounds are useful as PDE4 inhibitors.

BACKGROUND OF THE INVENTION

WO 2011/160632 discloses benzodioxole and benzodioxepene heterocyclic compounds useful as PDE4 inhibitors as well as suitable methods for the preparation thereof.

WO 2008/104175 discloses benzodioxole and benzodioxepene heterocyclic compounds useful as PDE4 inhibitors as well as suitable methods for the preparation thereof.

WO 2008/077404 discloses substituted acetophenones useful as PDE4 inhibitors as well as suitable methods for the preparation thereof.

WO 2015/197534 discloses methods for the preparation of 1,3-benzodioxole heterocyclic compounds.

WO 2017/103058 discloses further methods for the preparation of 1,3-benzodioxole heterocyclic compounds.

Zafrani et al. *Tetrahedron* 65, 2009, pp 5278-5283, describes a method for the difluoromethylation of phenols and thiophenols.

Sperry et al *Org. Process Res. Dev.* 15, 2011, pp 721-725, also describes the difluoromethylation of phenols.

Frey et al. *Tetrahedron* 2003, 59, pp. 6363-6373 also describes the demethylation and difluoromethylation of phenols Zhang et al. *J. Org. Chem.* 2006, 71, 9845-9848 also describes the difluoro-methylation of phenols.

Zheng et al. *Chem. Commun.* 2007, 5149-5151 also describes the difluoromethylation of phenols.

In the development of new drug candidates, it is highly desirable to have access to alternative methods for the preparation of the drug candidates, as some efficient small-scale synthesis may turn out to be difficult to up-scale to production scale quantities. Also, small-scale syntheses may involve reagents and solvents which are not feasible to utilize at a production scale level.

Hence, it is an object of the present invention to provide alternative methods for the preparation of 1,3-benzodioxole heterocyclic compounds of the type disclosed in WO 2011/160632, WO 2015/197534 and WO 2017/103058, insofar that such alternative methods provide advantages with respect to one or more features like the number of reactions steps, purity, yield, ease of purification, process economy, availability of starting materials and reagents, safety, predictability, etc.

Compared to step (2a) of WO 2017/103058 in step (2a) of the present invention, cheaper reagents and more environmentally benign solvents were used and the solution was heated to reflux and stirred until the conversion was ≥98%.

In step (3), when performing the reaction as described in Example 3 of WO 2017/103058 (Example 5 of the present invention), carbon dioxide is released in equimolar amounts to added amount of sodium chlorodifluoro acetate to the reaction. Upon scale-up gas-release and possible pressure increase in used equipment may turn the procedure into a potential safety issue. Therefore, an alternative procedure was developed in order to be able to control carbon dioxide release over time.

The identification of a by-product in present step (3) has led to new reaction conditions as said by-product is not removed during regular work-up and isolation of the compound. The use of TFA (trifluoroacetic acid) or MSA (methane sulfonic acid) in a polar solvent, at elevated temperature and subsequent removal by treatment with an aqueous base, such as NaOH or KOH during crystallization leads to a purity of >94% of the compound.

The identification of an impurity in present step (4) has led to new reaction conditions. The use of a solvent of DMF/tBuOH and a base of tert-BuOK suppressed the formation of impurity to a minimum, which afforded 70-73% isolated yield. This surpasses the yield of 57% as obtained by the method as in described in WO 2017/103058.

The improved yield, avoidance of potential safety issues, the use of other reaction conditions and the use of cheaper reagents optimizing the process economy of the process of the present invention as compared to the method as described in WO 2017/103058, WO 2011/160632 and WO 2015/197534, are quite surprising.

SUMMARY OF THE INVENTION

It has been found by the present inventors that alternative steps and use of alternative reagents disclosed herein provides advantages over the known methods by an improved overall chemical and volumetric yield, avoidance of potential safety issues and reduced cost for the production.

Hence, the present invention provides a method for the preparation of 1,3-benzo-dioxole compounds, e.g. a compound of formula (I).

Also within the scope of the invention are intermediates used in the foregoing method for preparing compounds of formula (I).

BRIEF DESCRIPTION OF DRAWING

The drawing is an X-ray powder diffraction pattern of crystalline Form E of 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone.

DETAILED DISCLOSURE OF THE INVENTION

In a first aspect, the present invention relates to a method for the preparation of a compound of formula (I)

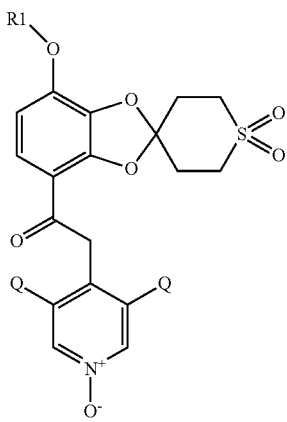

(I)

Wherein $R_1$ is selected from $CHF_2$ and $CF_3$, and Q is selected from chloro, bromo and fluoro.

In the compound of formula (I), $R_1$ is typically $CHF_2$. Q is typically selected from chloro, bromo and fluoro, preferably chloro, where the Q's preferably are the same. In one embodiment, both Q's are chloro.

DEFINITIONS

The term "$C_{1-6}$-alkyl" is intended to mean a saturated, straight or branched hydrocarbon chain having from one to six carbon atoms, including methyl, ethyl, propyl, isopropyl, butyl, isobutyl, secondary butyl, tertiary butyl, pentyl, isopentyl, neopentyl, tertiary pentyl, hexyl and isohexyl. In some embodiments, "$C_{1-6}$-alkyl" is a $C_{1-4}$-alkyl group, e.g. methyl, ethyl, propyl, isopropyl, butyl, isobutyl, secondary butyl and tertiary butyl. Correspondingly, "$C_{1-3}$-alkyl" includes methyl, ethyl, propyl and isopropyl.

The term "halogen" is intended to mean one of fluoro, chloro, bromo and iodo. In one embodiment, the term "halogen" designates fluoro or chloro. In another embodiment, the term "halogen" designates chloro.

The term "aryl" is intended to mean a carbocyclic aromatic ring system derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, and biphenyl. Preferred "aryl" is phenyl, naphthyl or indanyl, in particular phenyl, unless otherwise stated.

The term "arylalkyl" is intended to mean an aryl radical as defined above covalently joined to an alkyl group, e.g. benzyl.

METHODS OF PREPARATION

It appears that the method provides advantages over the known methods by relying on cheap starting materials, ease of the production method, and increasing yields in the reactions.

Step (1)

The method for the preparation of a compound of the formula (I) includes the formation of a compound of the formula (IV) which is obtained by reacting a compound of formula (II)

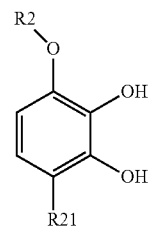

(II)

wherein $R_2$ is selected from hydrogen, $C_{1-6}$-alkyl and arylalkyl, $R_{21}$ is selected from hydrogen and $C(O)R_{22}$, and $R_{22}$ is selected from hydrogen and $C_{1-6}$-alkyl; with a compound of formula (III)

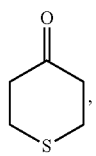

(III)

in the presence of an acid catalyst to form a compound of formula (IV)

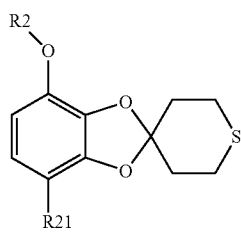

(IV)

wherein $R_2$ and $R_{21}$ is as defined above.

The acid catalyst is typically in the form of a clay or a zeolite. A zeolite is typically selected from CBV 720, CBV 760, CBV 780, HSZ-390HUA. A clay is typically selected from Montmorillonite K10, Taiko Classic, Taiko Omega, Actol-10, Actol-20, Actol-20X, Tonsil Supreme 116 FF or Tonsil Supreme 115 FF. In one embodiment, a clay is selected from Montmorillonite K10, Tonsil Supreme 116 FF or Tonsil Supreme 115 FF. In another embodiment, the clays is Montmorillonite K10.

The ratio between the zeolite or the clay and compound of formula (II) may have influence on the conversion and filtration-time. Hence, it is typically preferred to have an amount of the zeolite or the clay of 10%-w/w to 500%-w/w compared to the compound of formula (II). In particular the amount of mineral should be of 25%-w/w to 75%-w/w. preferably in the range 45%-w/w to 55%-w/w.

The reaction is typically conducted in toluene, benzene, 2-Methyl-THF (2-methyl-tetrahydrofuran), EtOAc (ethyl acetate), xylenes, heptane, octane, chlorbenzene and dichlorbenzene. In one embodiment, the solvent is toluene or xylenes. In another embodiment, the solvent is toluene.

The reaction is typically conducted at a temperature above 80° C. in order to promote the reaction. Hence, it is typically preferred that the temperature is in the range of 80-200° C., such as in the range of 100-160° C., especially at 105-115° C. or 135-145° C. In one embodiment, the reaction is performed at reflux of the reaction mixture. The reaction is typically allowed to proceed for 4-96 hours, such 24-84 hours, especially 48-84 hours.

The resulting compound of formula (IV) may be recovered by conventional means, known to those skilled in the art, e.g. by aqueous workup followed by extraction and finally precipitation and filtration.

In one embodiment of the invention, the compound of formula (II) is wherein $R_2$ is selected from hydrogen or methyl and $R_{21}$ is selected from hydrogen, $COCH_3$ or COOH. In another embodiment, the compound of formula (II) is 1-(2,3-dihydroxy-4-methoxyphenyl)ethanone.

In one embodiment of the invention, the compound of formula (III) is tetrahydrothiopyran-4-one.

In one embodiment of the invention, the compound of formula (IV) is wherein $R_2$ is hydrogen, methyl, ethyl, propyl, isopropyl, isobutyl, secondary butyl, tertiary butyl or benzyl, and $R_{21}$ is selected from hydrogen, $COCH_3$ or COOH. In another embodiment the compound of formula (IV) is wherein $R_2$ is methyl and $R_{21}$ is $COCH_3$.

Step (2a)

The compound of the formula (IV)

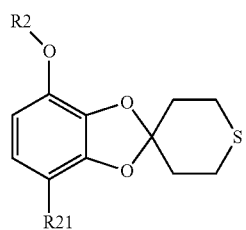

(IV)

wherein $R_2$ and $R_{21}$ is as defined above, is converted to a compound of formula (VI)

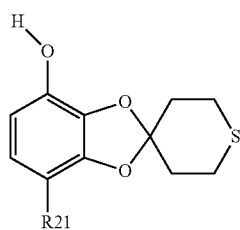

(VI)

wherein $R_{21}$ is defined above by deprotecting the phenol moiety.

This may be done by reacting the compound of formula (IV) with an aromatic or aliphatic thiol in combination with a base.

The aromatic thiol may be e.g., but is not limited to, benzenethiol, 4-methylbenzene-thiol, 3,5-dimethylbenzenethiol, 2,5-dimethylbenzenethiol, 4-isopropylbenzenethiol, or 5-tert-butyl-2-methyl-benzenethiol. In one embodiment, the aromatic thiol is 5-tert-butyl-2-methylbenzenethiol.

The aliphatic thiol may be e.g, but is not limited to, 1-dodecanethiol, 1-tetra-decanethiol, 1-hexadecanethiol, or tert-dodecanethiol. In one embodiment, the aliphatic thiol is 1-dodecanethiol.

The deprotection of the phenol group in step (2a) may be conducted using various solvents, e.g. selected from DMF (N,N-dimethylformamide), NMP (N-methyl-pyrrolidone), DMSO (dimethyl sulfoxide), methanol, ethanol, 1-propanol, 2-propanol and mixtures hereof. In one embodiment, the solvent is DMF. In another embodiment, the solvent is a mixture of DMF and methanol. In another embodiment the solvent is ethanol. In yet another embodiment, the solvent is 1-propanol.

The deprotection of the phenol group is performed in the presence of a base, e.g. selected from $K_2CO_3$, $Na_2CO_3$, $KHCO_3$, $NaHCO_3$, $CsCO_3$, TEA (triethylamine), a metal hydroxide, e.g. selected from NaOH, KOH and LiOH; and potassium tert-butoxide, tert-BuOLi (lithium tert-butoxide), sodium methoxide, sodium ethoxide, and DIPEA (N,N-diisopropylethylamine). In one embodiment, the base is $K_2CO_3$. In another embodiment, the base is sodium methoxide. In another embodiment the base is a metal hydroxide, In another embodiment the base is NaOH.

The reaction is typically conducted at a temperature in the range of 50-120° C., such as in the range of 70-100° C. The reaction is typically allowed to proceed for 2-36 hours, such as 3-24 hours. The reaction is typically allowed to proceed until the conversion is ≥98%.

In a specific embodiment of the present invention a mixture of the compound of formula (IV), a metal hydroxide, 1-dodecanethiol and an alcohol are heated to reflux and stirred. In another specific embodiment of the present invention the metal hydroxide is NaOH and the alcohol is EtOH. In another specific embodiment of the present invention, the metal hydroxid is NaOH and the alcohol is 1-propanol.

The resulting compound of formula (VI) may be recovered by conventional means, known to those skilled in the art, e.g. by aqueous workup followed by extraction and finally precipitation and filtration.

In one embodiment of the invention, the compound of formula (VI) is wherein $R_{21}$ is $C(O)R_{22}$, and $R_{22}$ is selected from hydrogen and $C_{1-6}$-alkyl. In another embodiment the compound of formula (VI) is 1-(7-hydroxyspiro[1,3-benzodioxole-2,4'-tetrahydro-thiopyran]-4-yl)ethanone.

Step (2b)

In step (2b) the compound of formula (VI) is reacted with aqueous $N(Bu)_4{}^+OH^-$ to form a compound of formula (VII)

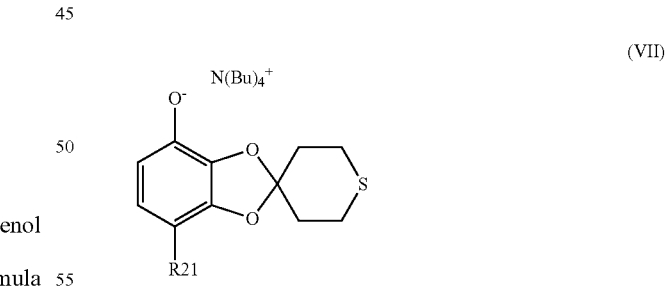

(VII)

wherein $R_{21}$ is as defined above.

The mixture is typically heated to a temperature in the range of 20-80° C., such as 55-65° C., until all has dissolved.

The resulting solution is typically washed with a solution of sodium chloride in water by stirring at a temperature in the range of 20-80° C., such as 55-65° C. for ≥20 min. Subsequently adding a mixture of water and sodium chloride followed by cooling of the mixture from ≥35° C. to 0-20° C., e.g. 5° C. over a period of 1-24 hours, such as 1-4 hours, causes the TBA (tetrabutylammonium) salt to precipitate. The TBA salt is isolated e.g. by filtration and dried.

Step (3)

The Compound of Formula (IX)

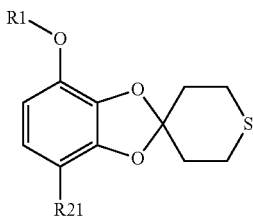

(IX)

wherein $R_1$ and $R_{21}$ are as defined above, may be obtained by alkylating the resulting compound of formula (VII)

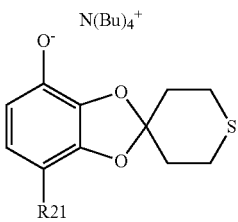

(VII)

wherein $R_{21}$ is as defined above, by reacting with a hydrochlorofluorocarbon reagent, $$R_1\text{—Cl} \qquad \text{(VIII)}$$

wherein $R_1$ is as defined above.

The alkylation may be conducted using one of various possible reagents, such as various hydrochlorofluorocarbon gases. In one embodiment, the alkylation reaction is conducted using chlorodifluoromethane in an aprotic polar solvent, e.g. selected from DMF (N,N-dimethylformamide), NMP (N-methylpyrolidone), DMI (1,3-dimethyl-2-imidazolidinone), DMSO (dimethyl sulfoxide), EtOAc (ethyl acetate), MeCN (acetonitrile) and THF (tetrahydrofuran), and mixtures hereof. In one preferred embodiment, the aprotic solvent is selected from DMF and NMP. In a particular embodiment, the reaction is conducted using chlorodifluoromethane in DMF.

The reaction is typically conducted at a temperature in the range of 40-120° C., such as in the range of 50-70° C. The reaction is typically allowed to proceed until ≤4% of the phenol is left in the reaction mixture.

The resulting compound of formula (IX) may be recovered by conventional means, known to those skilled in the art, e.g. by aqueous workup followed by precipitation and subsequently filtration.

In one embodiment of the invention, the compound of the formula (IX) is 1-[7-(difluoromethoxy)spiro[1,3-benzodioxole-2,4'-tetrahydrothiopyran]-4-yl]ethanone.

Alternative Step (2b+3)

Alternatively, the compound of formula (IX),

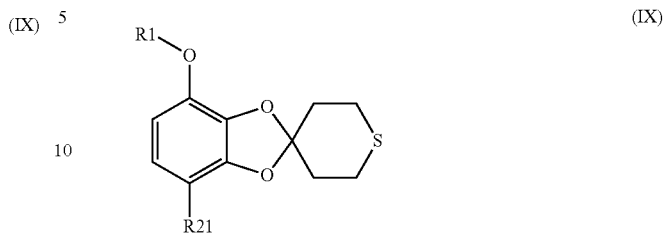

(IX)

wherein $R_1$ and $R_{21}$ are as defined above, may be obtained from the compound of formula (VI),

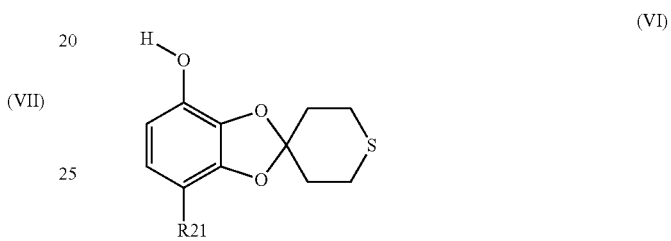

(VI)

wherein $R_{21}$ is defined above, without forming the intermediate salt of the formula (VII), by using a difluoromethylating reagent in a polar solvent in the presence of a base.

The difluoromethylating reagent is selected from e.g., but not limited to, sodium chlorodifluoroacetate, sodium bromodifluoroacetate, diethyl bromodifluoromethyl-phosphonate, chlorodifluoromethyl phenyl sulfone, and 2-chloro-2,2-difluoroaceto-phenone. Those skilled in the art can easily choose other suitable analogous of the mentioned difluoromethylating reagent. In one embodiment, the difluoromethylating reagent is sodium chlorodifluoroacetate. In another embodiment, the difluoro-methylating reagent is diethyl bromodifluoromethylphosphonate.

The reaction is performed in a solvent selected from e.g. DMF (N,N-dimethylform-amide), NMP (N-methylpyrolidone), DMI (1,3-dimethyl-2-imidazolidinone), DMSO (dimethyl sulfoxide), EtOAc (ethyl acetate), MeCN (acetonitrile), THF (tetrahydro-furan), ethanol, methanol, water, and mixtures hereof. In one embodiment, the solvent is a mixture of water and DMF. In another embodiment, the solvent is a mixture of water and acetonitrile.

The reaction is performed in the presence of a base selected from e.g. $K_2CO_3$, $Na_2CO_3$, $KHCO_3$, $NaHCO_3$, $CsCO_3$, TEA (triethylamine), tert-BuOLi (lithium tert-butoxide), sodium methoxide, sodium ethoxide, DIPEA (N,N-diisopropylethylamine), KOH, NaOH, LiOH. In one embodiment, the base is $K_2CO_3$. In another embodiment, the base is NaOH.

The reaction is typically conducted at a temperature in the range of 0-120° C., such as 6-115° C. In one embodiment, the reaction is performed at 6-20° C. using diethyl bromodifluoromethylphosphonate as difluoromethylating reagent. In another embodiment, the reaction is performed at ambient temperature to 111° C. using sodium chlorodifluoroacetate as difluoromethylating reagent.

When performing the above reaction as described in present Example 5, carbon dioxide is released in equimolar amounts to added amount of sodium chlorodifluoro acetate to the reaction. Upon scale-up gas release and possible pressure increase in used equipment may turn the procedure into a potential safety issue.

Therefore, an alternative procedure was developed in order to be able to control carbon dioxide release over time from the reaction.

Alternative Step (2b+3')

Alternatively, the compound of formula (IX),

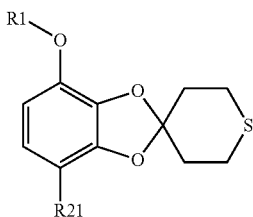

(IX)

wherein $R_1$ and $R_{21}$ are as defined above, may be obtained from the compound of formula (VI),

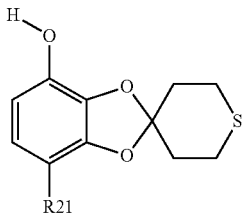

(VI)

wherein $R_{21}$ is defined above, by addition of a solution of the compound of formula (VI) and sodium chlorodifluoro acetate in DMF to a pre-heated mixture of DMF, water and potassium carbonate over an extended period of time; as described in present Example 8.

In one embodiment of the invention, the compound of the formula (IX) is 1-[7-(difluoromethoxy)spiro[1,3-benzodioxole-2,4'-tetrahydrothiopyran]-4-yl]ethanone.

The resulting compound of formula (IX), wherein $R_1$ and $R_{21}$ are as defined above, may be recovered by conventional means, known to those skilled in the art, e.g. by aqueous workup followed by precipitation and subsequently filtration.

During the reaction of forming the compound of formula (IX), a by-product of formula (IXb) is formed in considerable amounts.

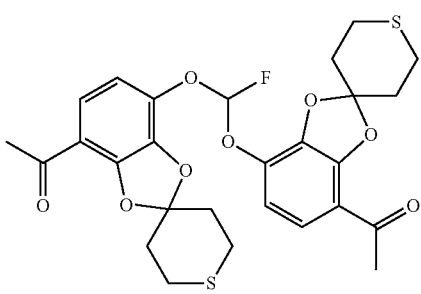

(IXb)

The by-product is hydrolyzed to the corresponding phenol which compound is then purged from the product by treatment with TFA or MSA in a polar solvent, such as DMF, at elevated temperature, and subsequent removal by treatment with an aqueous base such as NaOH or KOH during crystallization of the compound of formula (IX).

Step (4)

In step (4), the compound of formula (IX) is reacted with a pyridine compound of formula (X)

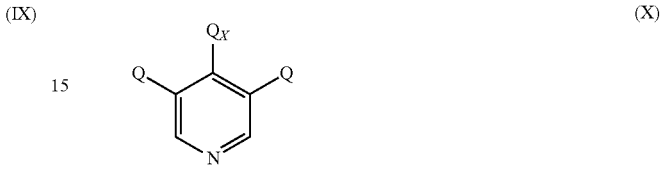

(X)

wherein Q is as defined above and $Q_x$ is selected from chloro, bromo, fluoro and iodo to form a compound of formula (XI)

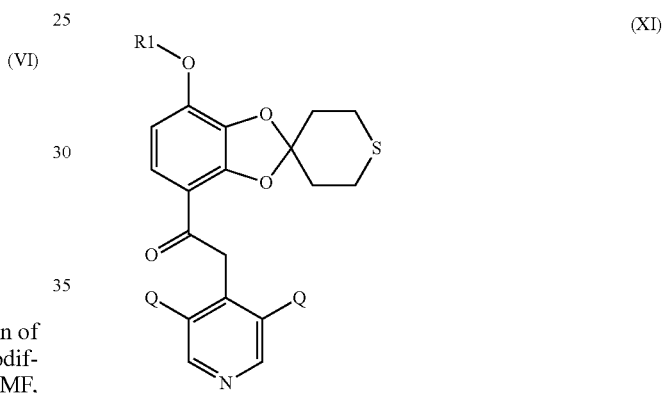

(XI)

wherein $R_1$ and Q are as defined above.

The pyridine coupling in step (4), is typically conducted in an polar solvent, e.g. selected from DMF (N,N-dimethylformamide), NMP (N-methylpyrrolidone), DMI (1,3-dimethyl-2-imidazolidinone), DMSO (dimethyl sulfoxide), MeCN (acetonitrile), THF (tetrahydrofuran), tBuOH (tert-butylalcohol) and mixtures hereof, in the presence of a base, e.g. selected from tert-BuOK (potassium tert-butoxide), tert-BuOLi (lithium tert-butoxide), tert-BuONa (sodium tert-butoxide), sodium or potassium methoxide, sodium or potassium ethoxide, $K_2CO_3$, $Na_2CO_3$, $KHCO_3$, $NaHCO_3$, $Et_3N$ (triethylamine) and DIPEA (N,N-diisopropylethylamine). In one embodiment, the solvent is DMF and the base is tert-BuOK.

Usually two equivalents or more of the base is used relative to the compound of the formula (IX), such as where the molar ratio (base)/(formula IX) is from 5:1 to 2:1, e.g. from 3:1 to 2:1, especially from 2.4:1 to 2.7:1.

The reaction in step (4) is typically conducted at a temperature of 0-40° C., such as 5-25° C.

In one embodiment of the invention, the compound of formula (X) is 3,4,5-trichloro-pyridine.

In one embodiment of the invention, the compound of formula (XI) is 2-(3,5-dichloro-4-pyridyl)-1-[7-(difluoromethoxy)spiro[1,3-benzodioxole-2,4'-tetrahydrothiopyran]-4-yl]ethanone.

During the reaction, an impurity of formula (XII) is formed in considerable amounts.

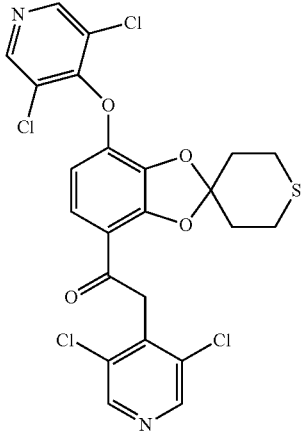

(XII)

This impurity is purged from the product by crystallising the product from a solvent selected from e.g. dimethylformamide (DMF), ethanol, methanol, ethyl acetate, hexane, heptane, and mixtures thereof. In one embodiment of the invention, the solvent is a mixture of ethyl acetate and ethanol.

During a detailed study of the reaction, an impurity of formula (XIIb) has been isolated in a significant amount.

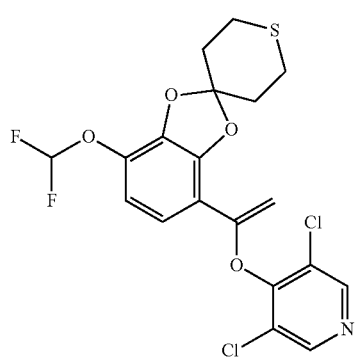

(XIIb)

The identification of impurity (XIIb) has led to new reaction conditions, as described below.

In Step (4), the solvent used was a DMF/tBuOH 30/70 v/v mixture and the base was tert-BuOK. Under these conditions the formation of impurity (XIIb) was suppressed to a minimum, while the reaction duration typically was 3-24 hours. The temperature range was 20-30° C. The new process afforded 70-73% isolated yield, surpassing the yield of 57% as obtained by the method as described in WO 2017/103058.

Step (5)

The oxidation of the resulting compound of formula (XI) is conducted to form the compound of formula (I)

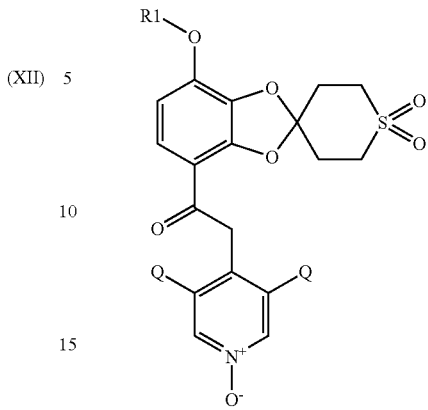

(I)

wherein $R_1$ and Q are as defined above, by reacting said compound of formula (XI) with an oxidation reagent.

The oxidation reagent is typically selected from PAA (peracetic acid) in AcOH (acetic acid), and $H_2O_2$ (aq) in formic acid or acetic acid. In one preferred embodiment, the oxidation reagent is PAA in AcOH. In one embodiment the amount of PAA used relative to (XI) (molar ratio) is typically 3 to 6, such as 3.8 to 4.2. The oxidation reagent is typically slowly added over a period of 1-8 hours, such as 3-5 hours, keeping the temperature in the range of 15-100° C., such as in the range of 15-50° C., especially in the range of 15-40° C.

The reaction is typically conducted at a temperature in the range of 30-70° C., such as 40-60° C., especially 48-55° C., and stirred for 3-48 hours, such as 16-24 hours.

Purification of the Compound of Formula (I)

The resulting crude product of formula (I) may advantageously be purified by crystallization, precipitation, chromatography or the like.

In one embodiment the resulting crude product of formula (I) is crystallized from a mixture of water and EtOH (ethanol), and isolated by filtration and dried.

In another embodiment, the first crystallization from water is skipped, and the compound of formula (I) is crystallized (form E) directly from the concentrated reaction mixture.

The crystalline form E of 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone has an X-ray powder diffraction pattern as appears in the drawing.

EXPERIMENTALS

Methods and Reagents

All chemicals and reagents used were available from commercial sources.

$^1$H nuclear magnetic resonance (NMR) spectra were recorded at the indicated magnetic field and chemical shift values ($\delta$, in ppm) are quoted in the specified solvent relative to tetramethylsilane ($\delta$=0.00).

HPLC: Column: Aeris Peptide 3.6 μm XB-C18, 100×4.6 mm, the eluent was a gradient of A: 10% MeCN; 90% H2O; 0.1% TFA and B: 90% MeCN; 10% H2O; 0.1% TFA, column temperature: 35° C., UV detection at 220 nm, flow rate: 1.5 mL/min. The following gradients of the eluents were used:

| Gradient steps 2a, 2b, 3, and 5 | | |
|---|---|---|
| Time (min) | % A | % B |
| 0 | 85 | 15 |
| 8 | 20 | 80 |
| 10 | 20 | 80 |
| 10 | 85 | 15 |
| 12.2 | 85 | 15 |

| Gradient Step 4 | | |
|---|---|---|
| Time (min) | % A | % B |
| 0 | 75 | 25 |
| 5 | 20 | 80 |
| 12.2 | 20 | 80 |
| 12.2 | 75 | 25 |
| 13.2 | 75 | 25 |

Example 1

Step (1): Preparation of 1-(7-methoxyspiro[1,3-benzodioxole-2,4'-tetrahydro-thiopyran]-4-yl)ethanone A reactor was charged with 1-(2,3-dihydroxy-4-methoxyphenyl)ethanone (60.0 kg, 329 mol), tetrahydrothiopyran-4-one (37.2 kg, 320 mol), Montmorillonite K 10 (30.0 kg), and toluene (720.0 L). The mixture was stirred with heating to reflux, applying a jacket temperature of 140-150° C. for 84 hours. The mixture was cooled to 86-90° C. and filtered through a bed of filter aid. The reactor was rinsed with hot (86-90° C.) toluene (120 L), and the hot toluene was then used to wash the bed of filter aid. The rinse of the reactor and the following wash of the bed of filter aid was repeated two times with hot toluene (120 L), and once with hot (70° C.) ethyl acetate (60 L). All the toluene and ethyl acetate filtrates were combined and cooled to 2-6° C. over approximately 6 hours. The mixture was stirred at 2-6° C. for approximately half an hour.

Unconverted starting material was collected by filtration, and dried in vacuo at 43-47° C. Yield 32.0 kg.

The filtrate from the isolation of unconverted starting material was cooled to 10-16° C. with stirring, and a mixture of sodium hydroxide (26.40 kg) and water (162.0 L) was added at 10-16° C. The reaction mixture was then stirred for approximately half an hour at 10-16° C., then the agitation was stopped, and the phases were allowed to settle. The lower aqueous phase was discarded, and then a mixture of sodium hydroxide (26.40 kg) and water (162 L) was added with stirring at 10-16° C. The mixture was stirred for approximately one hour, then agitation was stopped, and the phases were allowed to settle. The lower aqueous phase was discarded and the organic phase was transferred to a container. The reactor was rinsed with toluene, and then the organic phase was transferred back to the reactor through a Cartridge filter.

The solution was concentrated as much as possible in vacuo applying a temperature of ≤70° C. Ethanol (90.0 L) was added, and the mixture was heated to 47-53° C., and stirred at that temperature for 10-15 minutes. Then the mixture was concentrated as much as possible in vacuo at a temperature ≤55° C. Ethanol (120.0 L) was added to the reactor, the mixture was heated to reflux with stirring, and water (90.0 L) was added with heating, keeping the mixture at reflux. The mixture was cooled to 2-8° C. over approximately 10 hours and stirred at that temperature for approximately half an hour.

The product was isolated by filtration, washed with a mixture of ethanol (30.0 L) and water (22.8 L), and dried in vacuo at 43-47° C. Yield 21.80 kg (24% but 51% if corrected for recovered starting material). $^1$H NMR (600 MHz, DMSO-d6) δ 7.30 (d, J=9.0 Hz, 1H), 6.75 (d, J=9.0 Hz, 1H), 3.88 (s, 3H), 2.91-2.84 (m, 2H), 2.84-2.77 (m, 2H), 2.49 (s, 3H), 2.30-2.22 (m, 2H), 2.22-2.12 (m, 2H).

Step (1) was repeated as necessary in order to produce the needed amount of 1-(7-methoxyspiro[1,3-benzodioxole-2,4'-tetrahydrothiopyran]-4-yl)ethanone.

Other catalysts was used in the process; the table below summarizes the yield of the reaction and the amount of recovered starting material when the above procedure was performed with a series of clays and zeolites.

| Catalyst | Supplier | Input starting material | Yield % | Recovered SM % |
|---|---|---|---|---|
| HSZ-390HUA | Tosoh Corp. | 20 g | 15 | 63 |
| CBV 720 | Zeolyst Int. | 20 g | 17 | 56 |
| CBV 760 | Zeolyst Int. | 150 g | 18 | 57 |
| CBV 780 | Zeolyst Int. | 50 g | 16 | 48 |
| Taiko Classic | Taiko Clay Group | 10 g | 9 | 61 |
| Taiko Omega | Taiko Clay Group | 10 g | 18 | 63 |
| Actol-10 | Ashapura Perfoclay ltd | 20 | 20 | 55 |
| Actol-20 | Ashapura Perfoclay ltd | 20 g | 20 | 56 |
| Actol-20X | Ashapura Perfoclay ltd | 150 g | 20 | 57 |
| Tonsil Supreme 116 FF | Clariant Produkte GmbH | 150 g | 41 | 33 |
| Tonsil Supreme 115 FF | Clariant Produkte GmbH | 100 g | 31 | 41 |

Step (2a): Preparation of 1-(7-hydroxyspiro[1,3-benzodioxole-2,4'-tetrahydro-thiopyran]-4-yl)ethanone A reactor was charged with 1-(7-methoxyspiro[1,3-benzodioxole-2,4'-tetrahydro-thiopyran]-4-yl)ethanone (26.0 kg, 92.7 mol), potassium carbonate (14 kg, 101 mol), dimethylformamide (104 L), and 5-tert-butyl-2-methyl-benzenethiol (26.8 kg, 149 mol). The mixture was heated with stirring to 85-92° C. until a conversion of ≥98% was achieved, as indicated by HPLC. The mixture was then cooled to 25° C., added water (104 L) and sodium hydroxide (28% in water, 21.4 kg), and stirred for ≥10 minutes. If pH of the mixture was below 12, more sodium hydroxide (28% in water) was added. Then toluene (65 L) was added, and stirring was continued for ≥15 minutes. The agitation was stopped, and the phases were allowed to settle. The phases were separated and the organic phase was discarded. The two lower aqueous phases were stirred with toluene (65 L) and the mixture was stirred for ≥15 minutes. The agitation was stopped, allowing the phases to settle. The phases were separated and the organic phase was discarded. The two aqueous phases were returned to the reactor and hydrochloric acid (18% in water, 67.6 kg) was added slowly with stirring in order to control the gas evolution. The resulting mixture was stirred for ≥10 minutes. More hydrochloric acid (18% in water, 10.2 kg) was added in order to achieve pH ≤6.

The temperature of the mixture was adjusted to 35-45° C. and kept there during the following extractions. Ethyl acetate (156 L) was added and the mixture was stirred for ≥30 minutes. The stirring was stopped, and the phases were allowed to settle. The phases were separated. The aqueous phase was stirred with ethyl acetate (78 L) for ≥30 minutes. The agitation was stopped, and the phases were allowed to settle. The aqueous phases was discarded. The two ethyl acetate phases were combined in the reactor and stirred with water (78 L) for 15 minutes. The stirring was stopped, and the phases were allowed to separate. The aqueous phase was discarded.

The organic phases were concentrated as much as possible with a jacket temperature of 50-60° C. and applying a vacuum. Then heptane (39 L) was added, and the resulting mixture was cooled to 5° C. with a rate of 0.10° C./h, and kept at that temperature for ≥3 hours. The title compound was isolated by filtration, washed with a cold (5° C.) mixture of ethyl acetate (10 L) and heptane (10 L), and dried in vacuo at 40-50° C. Yield 19.75 kg (80%). $^1$H NMR (600 MHz, DMSO-d6) δ 10.51 (s, 1H), 7.18 (d, J=9.0 Hz, 1H), 6.50 (d, J=9.0 Hz, 1H), 2.93-2.85 (m, 2H), 2.84-2.78 (m, 2H), 2.46 (s, 3H), 2.31-2.23 (m, 2H), 2.20-2.11 (m, 2H).

Step (2b): Tetrabutylammonium 7-acetylspiro[1,3-benzodioxole-2,4'-tetrahydro-thiopyran]-4-olate 1-(7-hydroxyspiro[1,3-benzodioxole-2,4'-tetrahydrothiopyran]-4-yl)ethanone (19.75 kg, 74.16 mol) was charged to a suitable reactor followed by tetrabutylammonium hydroxide (40% solution in water, 53.0 kg, 81.7 mol). The jacket temperature was set to 60° C. and the mixture was stirred until all had dissolved. A saturated solution of sodium chloride in water (59.2 kg) was added and stirring was continued with a jacket temperature of 60° C. for ≥20 minutes. The agitation was stopped, allowing the phases to separate. The lower aqueous phase was discarded. The mixture in the reactor was stirred again with a jacket temperature of 60° C. A saturated solution of sodium chloride in water (29.6 kg) and then water (25 L) were added. The mixture was stirred for ≥15 minutes at a temperature ≥35° C. in the mixture. The mixture was cooled to 0-5° C. at a rate of approximately 20° C./hr, the mixture was seeded at 40° C. and again at 35° C. The mixture was stirred at 0-5° C. for ≥2 hours, and then the title compound was isolated by filtration and dried in vacuo at 40-50° C. Yield 32.9 kg (87%). $^1$H NMR (600 MHz, DMSO-d6) δ 6.94 (d, J=9.1 Hz, 1H), 5.74 (d, J=9.1 Hz, 1H), 3.23-3.07 (m, 8H), 2.87-2.72 (m, 4H), 2.25 (s, 3H), 2.16-2.07 (m, 2H), 2.06-1.96 (m, 2H), 1.62-1.51 (m, 8H), 1.30 (h, J=7.4 Hz, 8H), 0.93 (t, J=7.4 Hz, 12H).

Step (3): 1-[7-(difluoromethoxy)spiro[1,3-benzodioxole-2,4'-tetrahydrothiopyran]-4-yl]ethanone Tetrabutylammonium 7-acetylspiro[1,3-benzodioxole-2,4'-tetrahydrothiopyran]-4-olate (32.93 kg, 64.85 mol) and dimethylformamide (198 L) were added to a reactor. The mixture was stirred until all had dissolved. Chlorodifluoromethane (39.5 kg, 457 mol) was added to the solution via a dip pipe on the reactor. The reaction mixture was heated to 50-55° C. and stirred until 4% of the starting material was left as indicated by HPLC. The reaction mixture was cooled to 20-25° C. and transferred to a container via a filter. The reactor and the solid in the filter were washed with dimethylformamide (10 L) which was added to the container as well.

Water (198 L) and sodium hydroxide (28% in water, 11.0 kg) were charged to the reactor and heated to 45-55° C. The reaction mixture in the container was added slowly to the reactor with stirring, keeping the temperature at 45-55° C. The mixture was then cooled to 5-10° C. and stirred at that temperature for hours. The product was isolated by filtration, washed with water (82 L), and dried in vacuo at 45-55° C. with a bleed of nitrogen. Yield 19.08 kg (94%). $^1$H NMR (600 MHz, DMSO-d6) δ 7.34 (t, J=73.1 Hz, 1H), 7.32 (d, J=9.1 Hz, 1H), 6.86 (d, J=9.1 Hz, 1H), 2.92-2.80 (m, 4H), 2.54 (s, 3H), 2.34-2.27 (m, 2H), 2.27-2.19 (m, 2H).

Step (4) 2-(3,5-dichloro-4-pyridyl)-1-[7-(difluoromethoxy)spiro[1,3-benzodioxole-2,4'-tetrahydrothiopyran]-4-yl]ethanone Dimethyl formamide (96 L) was charged to a suitable reactor followed by addition of potassium tert-butoxide (17.60 kg, 156.8 mol). Transfer of potassium tert-butoxide was ensured with a rinse of dimethyl formamide (3 L), and the mixture was stirred until potassium tert-butoxide had dissolved. The solution was transferred from the reactor to a container, the reactor was rinsed with dimethyl formamide (6 L), which was transferred to the container as well.

The reactor was charged with 1-[7-(difluoromethoxy)spiro[1,3-benzodioxole-2,4'-tetrahydrothiopyran]-4-yl]ethanone (19.08 kg, 60.32 mol), 3,4,5-trichloropyridine (14.30 kg, 78.38 mol), and dimethylformamide (96 L). The mixture was stirred and cooled to 10-15° C., and then the solution of potassium tert-butoxide in dimethyl-formamide was added slowly, keeping the temperature of the reaction mixture at 5-25° C. The transfer of the potassium tert-butoxide solution was ensured with a rinse of dimethyl formamide (6 L). The mixture was heated to 20-25° C. and stirred until the conversion was ≥98% as indicated by HPLC.

Water (96 L) was added slowly with cooling to the reaction mixture keeping the temperature between 20-30° C. This was followed by the addition of saturated sodium chloride in water (115.2 kg) and ethyl acetate (134 L). The mixture was stirred for 20-60 minutes and then the agitation was stopped, allowing the phases to settle. The phases were separated, and the aqueous phase was returned to the reactor. Ethyl acetate (96 L) was added, and the mixture was stirred for 20-60 minutes. The agitation was stopped, allowing the phases to settle. The phases were separated. The organic phases were combined in the reactor and stirred with water (48 L) and saturated sodium chloride in water (57.8 kg) for ≥20 minutes. The agitation was stopped allowing the phases to settle. The lower aqueous phase was discarded, and water (48 L) and saturated sodium chloride (57.6 kg) were added. The mixture was agitated for 20-60 minutes, and then the agitation was stopped, allowing the phases to settle. The lower aqueous phase was discarded, and water (84 L) and sodium hydroxide (28% in water, 14.0 kg) were added. The mixture was stirred for 20-60 minutes and then the agitation was stopped, allowing the phases to settle. The lower aqueous phase was discarded.

The organic phase in the reactor was concentrated by use of vacuum and heating with a jacket temperature of 50-65° C. to a residual volume of approximately 40 L. Ethanol (57 L) was charged to the reactor, and the mixture was heated to reflux until a clear solution was obtained. The mixture was cooled to 5° C. over ≥5 hours and stirred at that temperature for ≥3 hours. The product was isolated by filtration, transfer was ensured with a rinse of ethanol (10 L). The product was washed with cold (≤5°) ethanol (48 L) and dried in vacuo at 45-55° C. Yield 15.57 kg (56%). $^1$H NMR (600 MHz, Chloroform-d) δ 8.52 (s, 2H), 7.46 (d, J=8.9 Hz, 1H), 6.80 (d, J=8.9 Hz, 1H), 6.73 (t, J=73.3 Hz, 1H), 4.59 (s, 2H), 3.01-2.85 (m, 4H), 2.47-2.30 (m, 4H). HPLC: Purity: 97.8%.

Step (5): 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone A reactor was charged with 2-(3,5-dichloro-4-pyridyl)-1-[7-(difluoromethoxy)-spiro[1,3-benzodioxole-2,4'-tetrahydrothiopyran]-4-yl]ethanone (15.6 kg, 33.7 mol) and glacial acetic acid (78.0 kg) and the mixture was cooled to 13-20° C. Per acetic acid (36-40% in acetic acid, 6.52 kg, 32.6 mol) was added slowly keeping the temperature below 40° C. The mixture was heated to 40-50° C. and stirred for 10-25 minutes. The mixture was cooled to 13-20° C. and a second portion of per acetic acid (36-40% in acetic acid, 6.51 kg, 32.5 mol) was added slowly keeping the temperature below 40° C. The mixture was heated to 40-50° C. and stirred for 10-25 minutes. The mixture was cooled to 20-30° C. and a third portion of per acetic acid (36-40% in acetic acid, 14.3 kg, 71.5 mol) was added slowly. The mixture was heated to 48-55° C. and stirred until the conversion was ≥98.5%. The mixture was cooled to 20-25° C. and a mixture of sodium metabisulphite (7.21 kg, 37.9 mol) and water (46 L) was added slowly keeping the temperature below 35° C.

2-propanol (78 L) was added and the mixture was heated to 60-65° C. and filtered hot. The reactor was cleaned and the filtrated reaction mixture was returned to the reactor. The mixture was heated to 60-65° C. and water (234 L) was added slowly keeping the temperature above 55° C. The mixture was stirred for 30-60 minutes at 60-65° C., cooled slowly to 5° C. over 12 hours, and stirred at 0-10° C. for ≥2 hours. The raw product was isolated by filtration, washed with water (27 L), and dried in vacuo for approximately two hours.

The solid was returned to the reactor and heated to reflux with ethanol (390 L). The mixture was then cooled to 68-72° C. and seeded. The mixture was cooled to 5° C. over 13 hours and stirred at 0-10° C. for ≥2 hours. The product was isolated by filtration, washed with a cold (0-10° C.) mixture of water (4 L) and ethanol (39 l), and dried in vacuo at 45-55° C. with a bleed of nitrogen. Yield 14.6 kg (85%). 1H NMR (600 MHz, Chloroform-d) δ 8.23 (s, 2H), 7.52 (d, J=9.1 Hz, 1H), 6.90 (d, J=9.1 Hz, 1H), 6.71 (t, J=72.3 Hz, 1H), 4.49 (s, 2H), 3.47-3.38 (m, 2H), 3.33-3.24 (m, 2H), 2.83-2.75 (m, 2H), 2.75-2.68 (m 2H). HPLC: purity 98.6%.

Example 2

1-(7-hydroxyspiro[1,3-benzodioxole-2,4'-tetrahydrothiopyran]-4-yl)ethanone

Sodium methoxide in methanol (30%, 64.2 mL, 0.34 mol) was added to a solution of 1-(7-methoxyspiro[1,3-benzodioxole-2,4'-tetrahydrothiopyran]-4-yl)ethanone (50.0 g, 0.178 mol) in dimethylformamide (250 mL) at 25-30° C. Then 1-dodecane-thiol (64.88 mL, 0.271 mol) was added at 25-30° C. and the mixture was heated to 95-100° C. for three hours. The reaction mixture was cooled to 25-30° C. and sodium hydroxide (28% in water, 50 mL) and water (250 mL) were added. The resulting mixture was stirred for half an hour and then the mixture was extracted with toluene (250 mL) three times. The aqueous solution was acidified with hydrochloric acid (6M) to approximately pH 6 and extracted with ethyl acetate (250 mL) four times. The ethyl acetate extracts were combined, washed with brine (250 mL) four times, and concentrated to approximately 50 mL using a rotary evaporator. Heptane (300 mL) was added and the mixture was stirred for one hour at ambient temperature. The product was isolated by filtration, washed with heptane (100 mL), and dried. Yield 44.3 g (93%). NMR complied with NMR of the product from step (2a) in Example 1.

Example 3

1-(7-hydroxyspiro[1,3-benzodioxole-2,4'-tetrahydrothiopyran]-4-yl)ethanone

Sodium hydroxide (31.4 g, 0.785 mol) was added to a solution of 1-(7-methoxy-spiro[1,3-benzodioxole-2,4'-tetrahydrothiopyran]-4-yl)ethanone (15.0 g, 53.5 mmol) in EtOH (500 mL) at 25-30° C. Then 1-dodecane-thiol (197 mL, 0.87 mol) was added at 25-30° C. and the mixture was heated to reflux and stirred for twenty four hours. From the reaction mixture was then removed 300 ml solvent under vacuum. To the remaining slurry was then added water (500 ml). The obtained solution was then extracted with toluene (500 ml). The organic phase was then discarded and remaining aqueous phase was acidified with hydrochloric acid (1M) to approximately pH 3-5. The product was isolated by filtration, washed with water (2×100 mL), and dried under vacuum at 60° C. Yield 93.0 g (98%). NMR complied with NMR of the product from step (2a) in Example 1

Example 4

1-(7-hydroxyspiro[1,3-benzodioxole-2,4'-tetrahydrothiopyran]-4-yl)ethanone

Sodium hydroxide (4.7 g, 117.7 mmol) was added to a solution of 1-(7-methoxy-spiro[1,3-benzodioxole-2,4'-tetrahydrothiopyran]-4-yl)ethanone (100.0 g, 0.357 mol) in 1-propanol (75 mL) at 25-30° C. Then 1-dodecane-thiol (29.5 mL, 123.1 mmol) was added at 25-30° C. and the mixture was heated to reflux and stirred for six hours. The reaction mixture was cooled to 25° C. Water (75 ml) was then added to the reaction mixture and then extracted twice with toluene (2×75 ml). The organic phases were then discarded and the remaining aqueous phase was acidified with hydrochloric acid (1M) to approximately pH 3-5. The product was isolated by filtration, washed with water (2×50 mL), and dried under vacuum at 60° C. Yield 11.3 g (79%). NMR complied with NMR of the product from step (2a) in Example 1

Example 5

1-[7-(difluoromethoxy)spiro[1,3-benzodioxole-2,4'-tetrahydrothiopyran]-4-yl]-ethanone A mixture of 1-(7-hydroxyspiro[1,3-benzodioxole-2,4'-tetrahydrothiopyran]-4-yl)ethanone (221.6 g, 0.8322 mol), potassium carbonate (161.3 g, 1.167 mol), sodium chlorodifluoroacetate (292.0 g, 1.915 mol), dimethylformamide (1.50 L), and water (500 mL) was stirred in a 5 liter reaction flask and heated slowly to 106-111° C., gas evolution was observed from approximately 78° C. The reaction mixture was stirred at 106-111° C. until the gas evolution had ceased, approximately two hours. The mixture was cooled with an ice-water bath, and water (1.00 L) was added slowly at 30-32° C. The resulting suspension was cooled further to 6° C. under stirring. The raw product was isolated by filtration and washed with water.

The wet raw product was stirred with ethyl acetate (1.66 L) and sodium hydroxide (1 M, 560 mL) for approximately 20 minutes, and then the phases was separated in a separatory funnel. The lower aqueous phase was discarded and the organic phase was washed twice with water (two times 560 mL). The organic phase was concentrated using a rotary evaporator (in vacuo with 60° C. in the water bath) to approximately 450 mL. Ethyl acetate (1.56 L) was added, and the mixture was concentrated again using a rotary evaporator as above to approximately 450 mL. Ethyl acetate (1.44 L) was added, and the unclear solution was filtered, transferring and washing with a fresh portion of ethyl acetate (100 mL). The combined filtrates were filtered through a plug of activated carbon (6.0 g), transferring and washing with ethyl acetate (200 mL). The combined filtrates were concentrated on a rotary evaporator as above to approximately 450 mL. The resulting hot solution (approximately 60° C.) was stirred at ambient temperature while heptane (2.00 L) was added slowly over approximately half an hour. The suspension was stirred at ambient temperature for 14 hours.

The mixture was stirred in an ice-water bath for approximately 2.5 hours, the temperature of the mixture was then 4° C. The product was isolated by filtration, washed with an ice-cold mixture of heptane and ethyl acetate (10:1, 200 mL), and dried in vauo at 50° C. with a bleed of air. Yield 201 g (76%). NMR complied with NMR of the product from step 3 in example 1.

Example 6

1-[7-(difluoromethoxy)spiro[1,3-benzodioxole-2,4'-tetrahydrothiopyran]-4-yl]-ethanone Sodium hydroxide (6.16 g, 154 mmol) was dissolved in water (40 mL) and the solution was stirred with cooling in an ice-water bath. 1-(7-hydroxyspiro[1,3-benzodioxole-2,4'-tetrahydrothiopyran]-4-yl)ethanone (2.00 g, 7.51 mmol) and acetonitril (20 mL) were added, and stirring with cooling was continued. Diethyl bromodifluoromethylphosphonate (2.67 mL, 15.0 mmol) was added in one portion at 6° C., and stirring with cooling was continued for approximately 20 minutes. The cooling bath was removed, and the mixture was stirred for approximately 21 hours at ambient temperature.

The phases were separated using a separatory funnel, and the water phase was extracted with ethyl acetate (20 mL). The combined organic phases were washed with water (20 mL) and then with brine (20 mL). The organic phase was concentrated to dryness using a rotary evaporator. Ethyl acetate (20 mL) was added to the residue, and the mixture was concentrated to dryness once again using the rotary evaporator.

The residue was dissolved in ethyl acetate (30 mL) and filtered, transferring and washing with ethyl acetate (20 mL). The combined filtrates were concentrated to dryness using a rotary evaporator as above, giving the title compound as a yellowish solid. Yield 2.14 g (90%). NMR complied with NMR of the product from step 3 in example 1.

Example 7

1-[7-(difluoromethoxy)spiro[1,3-benzodioxole-2,4'-tetrahydrothiopyran]-4-yl]-ethanone Sodium hydroxide (301 g, 7.52 mol) was stirred with water (2.0 L), and the resulting solution was cooled with an ice-water bath. 1-(7-hydroxyspiro[1,3-benzodioxole-2,4'-tetrahydrothiopyran]-4-yl)ethanone (100.1 g, 0.3757 mol) and acetonitrile (1.0 L) were added. Diethyl bromodifluorophosphonate (150.5 g, 0.5637 mol) was added slowly over approximately 40 minutes at a temperature of 15-20° C. in the reaction mixture. Stirring was continued for another approximately two hours at 15-20° C. The phases were separated.

Water (920 mL) was added slowly to the organic phase with stirring and the resulting suspension was stirred at ambient temperature for approximately 18 hours. The product was isolated by filtration, washed with a 1:1 mixture of acetonitrile and water (120 mL), and dried in vacuo at 50° C. with a bleed of air. Yield 108 g (91%). NMR complied with NMR of the product from step 3 in example 1.

Example 8

1-[7-(difluoromethoxy)spiro[1,3-benzodioxole-2,4'-tetrahydrothiopyran]-4-yl]-ethanone To a mixture of potassium carbonate (1.45 g, 10.5 mmol) in DMF (8.2 mL) and water (3.6 mL) at a reaction temperature of 110° C. was slowly added a solution of 1-(7-hydroxyspiro[1,3-benzodioxole-2,4'-tetrahydrothiopyran]-4-yl)ethanone (2.0 g, 7.51 mmol) and sodium chlorodifluoro acetate (2.86 g, 18.8 mmol) in DMF (6.2 mL) over a period of 2-4 h. After completion of addition the reaction mixture was stirred for another 60 min. The reaction temperature was then brought down to 70° C. where an aqueous 0.5M NaOH solution (10 mL) was added to the reaction mixture.

The obtained reaction slurry was then slowly cooled down to 10-20° C. The product was isolated by filtration, washed with water (40 mL), and dried under vacuum at 60° C. Yield 1.73 g (73%). NMR complied with NMR of the product from step (3) in Example 1.

Example 9

2-(3,5-dichloro-4-pyridyl)-1-[7-(difluoromethoxy)spiro[1,3-benzodioxole-2,4'-tetrahydrothiopyran]-4-yl]ethanone Dimethyl formamide (128 mL) and tert-butanol (298 mL) were charged to a suitable reactor followed by addition of potassium tert-butoxide (81.4 g, 726 mmol). The mixture was stirred until potassium tert-butoxide had dissolved.

A second reactor was charged with 1-[7-(difluoromethoxy)spiro[1,3-benzodioxole-2,4'-tetrahydrothiopyran]-4-yl]ethanone (85.0 g, 269 mmol), 3,4,5-trichloropyridine (58.8 g, 322 mmol), dimethylformamide (76.5 mL) and tert-butanol (179 mL). The mixture was stirred at 22-25° C., when the solution of potassium tert-butoxide in dimethylformamide and tert-butanol was added slowly, keeping the temperature of the reaction mixture <30° C. The reaction mixture was stirred at 22-25° C. until the conversion was ≥98% as indicated by HPLC.

Water (340 mL) was added slowly to the reaction mixture keeping the temperature <30° C. The reaction mixture was transferred to a separatory funnel and diluted with ethyl acetate (850 mL). The aqueous lower phase was discarded. The organic phase was washed with an aqueous sodium hydroxide solution (2M, 500 mL), and the aqueous lower phase was discarded. The organic phase was washed with water (340 mL) and the aqueous lower phase was discarded. The organic phase was transferred to a suitable reactor and concentrated under reduced pressure (100 mbar) at 50° C.

(jacket temperature) until the temperature of the vapor reached 39° C. Then ethanol (255 mL) was added and the slurry was heated to reflux (90° C.) and stirred for one hour. Then the solution was cooled slowly to 5° C. The product was isolated by filtration, transfer was ensured with a rinse of ethanol (20 mL). The product was washed with cold (≤5°) ethanol (150 mL) and dried in vacuo at 45-55° C. Yield 91.0 g (73.2%). $^1$H NMR (600 MHz, Chloroform-d) δ 8.52 (s, 2H), 7.46 (d, J=8.9 Hz, 1H), 6.80 (d, J=8.9 Hz, 1H), 6.73 (t, J=73.3 Hz, 1H), 4.59 (s, 2H), 3.01-2.85 (m, 4H), 2.47-2.30 (m, 4H). HPLC: Purity: 97%.

Example 10

Preparation of 1-(7-hydroxyspiro[1,3-benzodioxole-2,4'-tetrahydrothiopyran]-4-yl)ethanone A suitable reaction vessel was flushed with nitrogen. The nitrogen flow was temporary stopped and 1-(7-methoxyspiro[1,3-benzodioxole-2,4'-tetrahydro¬thiopyran]-4-yl) ethanone (1.00 kg, 3.57 mol) was charged to the reaction vessel followed by ethanol (2.5 L), sodium hydroxide (314 g, 7.85 mol, 2.2 eq), and 1-dodecanethiol (1.66 kg, 8.2 mol, 2.3 eq). The reaction mixture was heated to refluxing conditions while agitated, and this temperature was maintained for 22-24 hours.

IPC (Ion Pair Chromatography) was prepared in ethanol for HPLC analysis (220 nm). If the starting material was present in less than 2 area %, the reaction mixture was cooled to 20-25° C.

Hereafter, water (5 L) was charged to the reaction mixture upon agitation. Toluene (1.5 L) was added subsequently, and the mixture was agitated for at least 15 minutes. The agitation was stopped and the phases were allowed to separate.

The aqueous phase was washed twice with toluene (2×1.5 L)

Water (1 L) was added followed by addition of an aqueous hydrochloric acid solution (18%, 1.5-1.6 kg, 2.1-2.2 eq).

The precipitate was filtered off and washed twice with water (2×2 L), and with heptane (2 L). The moist solid was transferred to the reaction vessel, and heptane (5 L) was added. The slurry was agitated and heated to refluxing conditions, with water being removed azeotropically.

The mixture was cooled to 20-25° C. and the solid was filtered off and dried in vacuum. Yield: 80-90%. NMR complied with NMR of the product from step (2a) in Example 1.

Preparation of 1-[7-(difluoromethoxy)spiro[1,3-benzodioxole-2,4'-tetrahydro-thiopyran]-4-yl]ethanone Potassium carbonate (3.12 kg, 22.6 mol, 1.4 eq) and DMF (15.8 kg) was added to a suitable reaction vessel (#1). The suspension was agitated at 20-25° C. and the vessel and mixture were flushed with nitrogen for at least 1 hour at 20-25° C.

In a separate reaction vessel (#2) equipped with a nitrogen bubble tube was placed 1-(7-hydroxyspiro[1,3-benzodioxole-2,4'-tetrahydro¬thiopyran]-4-yl)ethanone (4.3 kg, 16.2 mol, 1 eq), and sodium chlorodifluoro acetate (6.16 kg, 40.4 mol, 2.5 eq), and DMF (12 kg). The suspension was agitated at 20-25° C. and the vessel and mixture were flushed with nitrogen for at least 1 hour at 20-25° C.

The suspension in vessel (#1) was heated to 115° C. and the content of vessel (#2) was transferred to vessel (#1) over the course of 7-8 h.

An IPC was prepared in acetonitrile for HPLC analysis (220 nm), with the criterion for further progress being: <5 area % of 1-(7-hydroxyspiro[1,3-benzodioxole-2,4'-tetrahydro¬thiopyran]4-yl)ethanone.

The reaction mixture was cooled to 20-25° C. and aqueous KOH solution (0.75 M, 18.8 kg) was added to the reaction.

The precipitate was filtered off and washed with KOH solution (0.75 M, 9 kg) followed by water (86 kg).

The moist material was dissolved in DMF (16 kg) and heated to 40-45° C. MSA (methane sulfonic acid) (3.44 kg, 35.8 mol, 2.2 eq) was added while maintaining the temperature between 45-50° C.

An IPC was prepared in acetonitrile for HPLC analysis (272 nm), with the criterion for further progress being: <4 area % of chemical byproduct of formula (IXb).

The reaction mixture was cooled to 35-40° C. and an aqueous KOH solution (3.25M, 18.7 kg) was added to the mixture. After complete addition, the mixture was cooled to 20-25° C. The criterion for further progress was a pH value of the solution of 10-12.

The solid was filtered off and washed with KOH solution (0.75 M, 9 kg) followed by water (86 kg). The solid was dried in vacuum at temperature of 60° C.

Yield: >85% (>93% purity). NMR complied with NMR of the product from step (3) in Example 1.

Alternatively, TFA can be used for work up instead of MSA. The moist material after first isolation was dissolved in DMF (100 ml). TFA (trifluoroacetic acid) (13.4 g, 116.4 mmol, 1.5-3 eq) was added together with water (21 mL), the reaction was performed at 60-70° C.

The reaction mixture was cooled to 44-50° C. and an aqueous NaOH solution (1.25M, 140 mL) was added to the mixture. After complete addition, the mixture was stirred for 1 h.

The solid was isolated by filtration and washed with 0.5M NaOH and then water (480 mL). The solid was dried in vacuum at temperature of 50° C. Yield: >90% (>94% purity). NMR complied with NMR of the product from step (3) in Example 1.

Preparation of 3,4,5-tricholoropyridine

Step 1: A stirred solution of 4-pyridinol (1.0 eq.) in acetonitrile (15.0 vol.) and water (0.1 vol.) was heated to 40° C. and then added N-chloro succinamide (2.2 eq.) in portions at 40-55° C. The reaction mixture was stirred for 6-8 h at 45-55° C., the progress of reaction was monitored by HPLC. After completion of the reaction the reaction were cooled and stirred for 3-4 h. The solid was filtered and washed with acetonitrile (1×2.0 vol.) and water (5.0 vol+2.0 vol). The product was dried in oven up to constant weight.

Step 2: To a stirred suspension of 3,5-dichloro-4-pyridinol (1.0 eq.) in acetonitrile (5.0 vol.) was added POCl$_3$ (2.0 eq.). The reaction mixture was heated to 50-55° C. and stirred for 24 hours. The progress of the reaction was monitored by HPLC. After completion of reaction, the mixture was cooled. Then reaction mixture was slowly poured into water (5.0 vol) at 2-10° C. The mixture was stirred for 20-30 minutes and pH was adjusted to 9-10 with 50% NaOH(aq). The temperature was raised to 25-30° C. and the mixture was extracted with n-heptane (1×18.0 vol., 2×10.0 vol.). The combined organic layers were washed with water (1×5.0 vol.) and then added charcoal (15% w/w) and stirred for 1-2 hours. The organic phase was filtered through hyflo bed and the filter cake was washed with heptane (2.0 vol). The collected organic phase was concentrated under vacuum at 40° C. or below until up to 1.0 vol present.

The mixture was cooled to 25-30° C. and water (2.0 vol) was added. The mixture was again concentrated under vacuum to remove more heptane. The concentration was stopped when less than 2.0 vol present. Water (5.0 vol) was added and the mixture was stirred for 2-3 h. The solid was isolated by filtration and washed with water (2.0 vol). Dried in vacuum oven at 40-45° C. until constant weight. 1H NMR (600 MHz, Chloroform-d) δ 8.52 (s, 2H)

Preparation of 2-(3,5-dichloro-4-pyridyl)-1-[7-(difluoromethoxy)spiro[1,3-benzodioxole-2,4'-tetrahydrothiopyran]-4-yl]ethanone DMF (5 L) was added to a reaction vessel and subsequently, potassium tert-butoxide (0.92 L, 0.8 mol, 2.6 eq) was added in portions upon efficient agitation. The mixture was agitated at 20-25° C. under inert atmosphere overnight. 1-[7-(difluoromethoxy)spiro[1,3-benzodioxole-2,4'-tetrahydrothiopyran]-4-yl]ethanone (1 kg, 3.16 mol, 1 eq) and 3,4,5-tricholoropyridine (0.73 kg, 4.1 mol, 1.3 eq) were added to a reaction vessel (#2) followed by DMF (4.5 L). The agitation was started at a rate that ensures good mixing of the reactants.

The solution of potassium tert-butoxide was added to vessel (#2).

When 1-[7-(difluoromethoxy)spiro[1,3-benzodioxole-2,4'-tetrahydrothiopyran]-4-yl]ethanone was <2%, the reaction mixture was cooled and added water (1 L) and ethyl acetate (10 L)

Water (19 L) was added and the mixture was agitated. The agitation was stopped, and the phases were allowed to separate. Temperature was kept at 35-45° C.

The lower aqueous phase was discarded. Ethyl acetate (5 L) was added followed by water (20 L). The mixture was agitated, and after agitation the phases were allowed to separate.

The lower aqueous phase was discarded. The organic phase was heated to refluxing conditions upon agitation. While at reflux, ethanol (15 L) was charged to the mixture, at a rate which allows the refluxing conditions to be maintained. The azeotropic solvent mixture was distilled off until the vapor temperature was 74-76° C.

The temperature of the mixture was cooled and the product was filtered off and washed twice with cold ethanol (2×2.5 L).

The product was dried in vacuum at 40-50° C. Yield: 45-80%. NMR complied with NMR of the product from step (4) in Example 1.

Preparation of 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone In an reaction vessel was placed 2-(3,5-dichloro-4-pyridyl)-1-[7-(difluoromethoxy)-spiro[1,3-benzodioxole-2,4'-tetrahydrothiopyran]-4-yl]ethanone (16.1 kg, 34.8 mol, 1 eq) and glacial acetic acid (33.8 kg). The suspension was cooled to 15-20° C. Peracetic acid (36-40%, 20.5 kg, 104.7 mol, 3.01 eq) was added to the mixture in portions. The mixture was heated to 60° C. and agitated for 12-24 hours.

An IPC was prepared in acetonitrile for HPLC analysis (220 nm). The reaction was done, when 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone>98.5 area %.

Acetic acid (36 kg) and sodium metabisulfite (2.415 kg, 12.7, 0.36 eq) was added to reaction mixture. The mixture was heated to 40-45° C. for at least 3 hours.

Acetic acid was removed by evaporation in vacuum and ethanol (386 L) was then added upon agitation followed by water (16 L).

The title compound (141 g, Form E) was added to the mixture, and the mixture was then heated to reflux.

The solid was filtered off, washed with ethanol (39 L), and dried in vacuum at 50° C. Yield: 80-90%). NMR complied with NMR of the product from step (5) in Example 1. The X-ray powder diffraction pattern appears in the drawing.

The invention claimed is:

1. A method for the preparation of a compound of formula (I)

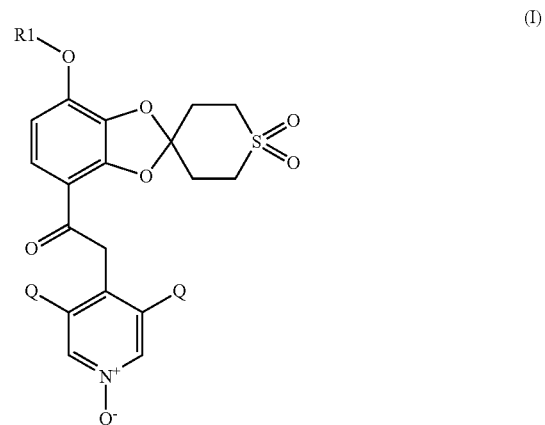

(I)

wherein $R_1$ is $CHF_2$ and Q is selected from chloro, bromo and fluoro, comprising:

(3') reacting the compound of formula (VI),

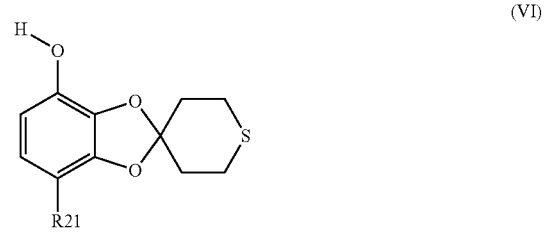

(VI)

wherein $R_{21}$ is $C(O)CH_3$, by addition of a solution of the compound of formula (VI) and sodium chlorodifluoro acetate in N,N-dimethylformamide (DMF) to a preheated mixture of DMF, water and potassium carbonate to obtain the compound of formula (IX),

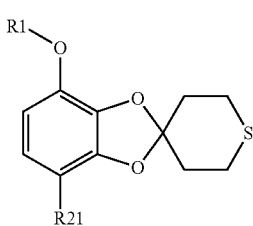

wherein $R_1$ and $R_{21}$ are as defined above; and a. (4) coupling the compound of Formula IX with a pyridine compound, and (5) oxidizing the compound of step (4) to form the compound of Formula (I);

or alternatively, b. (4') oxidizing the compound of Formula IX, and (5') coupling the compound of step (4') with a pyridine compound to form the compound of Formula (I); and wherein the reaction in (3') further comprises treating the compound of formula (IX) with trifluoracetic acid (TFA) or methansulfonic acid (MSA) in DMF at elevated temperature and subsequent removal by treatment with an aqueous base during crystallization of the compound of formula (IX).

2. The method according to claim 1, wherein the aqueous base is selected from KOH and NaOH.

3. The method according to claim 1, wherein the mixture of DMF, water and potassium carbonate is pre-heated to a temperature of about 110° C.

4. The method according to claim 1, wherein the solution of the compound of formula (VI) and sodium chlorodifluoro acetate in N,N-dimethylformamide (DMF) is added to a pre-heated mixture of DMF, water and potassium carbonate over a period of about 2 to about 4 hours.

5. The method according to claim 1 wherein the coupling the compound of Formula (IX) with a pyridine compound comprises (4) reacting the compound of formula (IX) with a pyridine compound of formula (X)

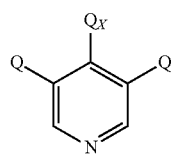

wherein Q is selected from chloro, bromo and fluoro, and $Q_x$ is selected from chloro, bromo, fluoro, and iodo, to form a compound of formula (XI);

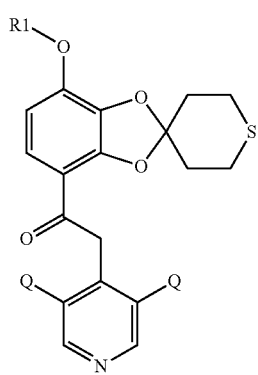

wherein $R_1$ is selected from $CHF_2$ and $CF_3$, and Q is as defined above.

6. The method according to claim 5, wherein the reaction in step (4) is conducted in a polar solvent selected from DMF (N,N-dimethylformamide), NMP (N-methylpyrrolidone), DMI (1,3-dimethyl-2-imidazolidinone), DMSO (dimethyl sulfoxide), MeCN (acetonitrile), THF (tetrahydrofuran), tBuOH (tert-butylalcohol) and mixtures thereof, in the presence of a base selected from tert-BuOK (potassium tert-butoxide), tert-BuOLi (lithium tert-butoxide), tert-BuONa (sodium tert-butoxide), sodium or potassium methoxide, sodium or potassium ethoxide, $K_2CO_3$, $Na_2CO_3$, $KHCO_3$, $NaHCO_3$, $Et_3N$ (triethylamine) and DIPEA (N,N-diisopropylethylamine).

7. The method according to claim 6, wherein the reaction in step (4) is conducted in a solvent of DMF/tBuOH and using tert-BuOK as base.

8. The method according to claim 7, wherein the solvent of DMF/tBuOH is a 30/70 v/v mixture.

9. The method according to claim 5, wherein the method further comprises the preparation of the compound of formula (X)

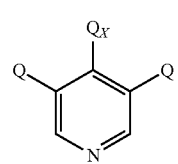

wherein each Q and $Q_x$ are chloro, comprising each of the steps:

(i) chlorinating 4-pyridinol with N-chloro succinamide to form 3,5-dichloro-4-pyridinol; and (ii) chlorinating 3,5-dichloro-4-pyridinol with $POCl_3$ to form the compound of formula (X).

10. The method according to claim 1 wherein the compound of Formula (VI) is prepared by a process comprising:
(2a) reacting the compound of formula (IV)

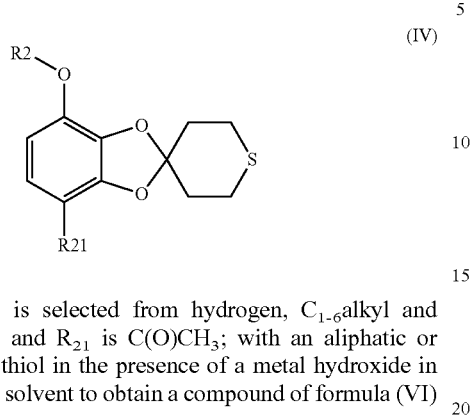

(IV)

wherein $R_2$ is selected from hydrogen, $C_{1-6}$alkyl and arylalkyl, and $R_{21}$ is $C(O)CH_3$; with an aliphatic or aromatic thiol in the presence of a metal hydroxide in a suitable solvent to obtain a compound of formula (VI)

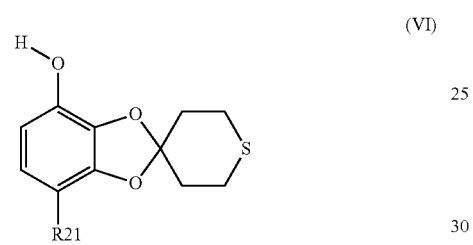

(VI)

wherein $R_{21}$ is as defined above.

11. The method according to claim 10, wherein the aromatic thiol is selected from benzenethiol, 4-methylbenzenethiol, 3,5-dimethylbenzenethiol, 2,5-dimethylbenzenethiol, 4-isopropylbenzenethiol, and 5-tert-butyl-2-methyl-benzenethiol.

12. The method according to claim 10, wherein the aliphatic thiol is selected from 1-dodecanethiol, 1-tetradecanethiol, 1-hexadecanethiol, and tert-dodecanethiol.

13. The method according to claim 10, wherein the solvent is selected from selected from DMF (N,N-dimethylformamide), NMP (N-methyl-pyrrolidone), DMSO (dimethyl sulfoxide), methanol, ethanol, 1-propanol, and 2-propanol, or mixtures thereof.

14. The method according to claim 10, wherein the metal hydroxide is sodium hydroxide.

15. The method according to claim 10, wherein in the reaction in (2a) the aliphatic thiol is 1-dodecanethiol, the solvent is an alcohol, and the mixture of the compound of formula (IV), metal hydroxide, 1-dodecanethiol and alcohol is heated to reflux and stirred.

16. The method according to claim 15 wherein the metal hydroxide is sodium hydroxide and the alcohol is ethanol.

17. The method according to claim 5, wherein the oxidizing the compound of step (4) comprises:
(5) oxidizing the compound of formula (XI)

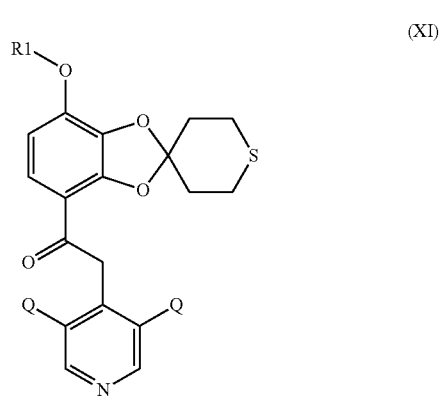

(XI)

with an oxidizing reagent to prepare the compound of formula (I)

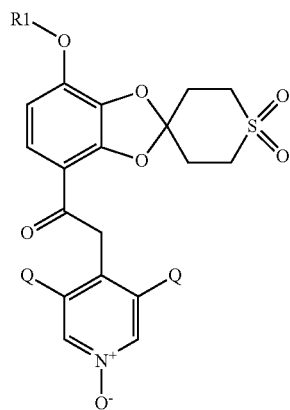

wherein $R_1$ is $CHF_2$, and Q is selected from chloro, bromo and fluoro.

18. The method according to claim 17, wherein the reaction in (5) the oxidizing agent is selected from PAA (peracetic acid) in AcOH (acetic acid), and $H_2O_2$ (aq) in formic acid or acetic acid.

19. The method according to claim 18, wherein the oxidizing agent is PAA in AcOH.

20. The method according to claim 17, wherein the reaction in (5) the compound of formula (I) is crystalized directly from the concentrated reaction mixture.

21. The method according to claim 1, wherein each Q is chloro.

* * * * *